United States Patent [19]

Albright

[11] 4,054,544

[45] Oct. 18, 1977

[54] FLAME RETARDANT POLYURETHANE COMPOSITION CONTAINING BIS(HALOALKYL)-NITRILO(TRIMETHYLENE PHOSPHONATES) AND PHOSPHONATE COMPOUND

[75] Inventor: James A. Albright, Ann Arbor, Mich.

[73] Assignee: Velsicol Chemical Corporation, Chicago, Ill.

[21] Appl. No.: 683,357

[22] Filed: May 5, 1976

[51] Int. Cl.² .......................... C08J 9/00; C07F 9/40
[52] U.S. Cl. .................. 260/2.5 AJ; 260/45.7 P; 260/932
[58] Field of Search .............. 260/932, 45.7 P, 2.5 AJ

[56] References Cited

U.S. PATENT DOCUMENTS

| | | | |
|---|---|---|---|
| 3,257,479 | 6/1966 | Irani, et al. | 260/932 |
| 3,711,577 | 1/1973 | Maier | 260/932 |

FOREIGN PATENT DOCUMENTS

| | | | |
|---|---|---|---|
| 1,175,041 | 12/1969 | United Kingdom | 260/932 |

*Primary Examiner*—Anton H. Sutto
*Attorney, Agent, or Firm*—Robert M. Phipps

[57] ABSTRACT

Compounds of the formula

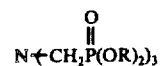

wherein each R is independently selected from the group comprising halogenated alkyl radicals having from about 2 to about 6 carbon atoms and from 1 to about 4 halogen substituents. Also, a polyurethane polymeric composition comprising a polyurethane polymer and a flame retarding amount of the above described compound.

10 Claims, No Drawings

FLAME RETARDANT POLYURETHANE COMPOSITION CONTAINING BIS(HALOALKYL)-NITRILO(TRIMETHYLENE PHOSPHONATES) AND PHOSPHONATE COMPOUND

BACKGROUND OF THE INVENTION

1. Field of the Invention

Compounds which are esters of phosphorus acids, wherein such compounds contain at least one P—O—C linkage, three phosphorus atoms, and wherein at least two of the phosphorus atoms are linked to each other by a carbon containing radical in which each phosphorus is attached directly to at least one carbon atom. The compounds within the scope of this invention are also flame retardants for polyurethane polymeric compositions.

2. Description of the Prior Art

During the past several years, a large number of flame retardants have been developed for use with an almost equally large number of flammable materials. Cellulosic materials (such as paper and wood) and polymeric materials (such as polyolefins, polyurethane, and polystyrene) are just two examples of materials for which flame retardants have been developed. For any class of flammable materials, such as synthetic type polymers, those skilled in the art have long been aware that some flame retardant additives are more effective in polymers and polymeric compositions than other flame retardant additives. This is because the efficacy of any flame retardant in polymers or polymeric compositions is measured not only by the flame retardant capability of the additive but also by the ability of the additive to improve or modify, or at least not to detract from, other physical or mechanical properties of the polymer or polymeric composition. The mere fact, therefore, that most flame retardants contain halogen and phosphorus atoms does not assure that any given halogenated or phosphorus-containing compound will impart usable flame retarding characteristics to all or even to any polymeric system. Furthermore, as those skilled in the art have improved the flame retardancy of many polymeric materials, they have been simultaneously required to provide the necessary flame retardancy with a minimal effect upon other properties of the polymer such as the light stability, processability, and flexural, tensile and impact strengths. Also, it has been the desire of those involved in the art of flame retardants to provide flame retardants having a durable lasting effect. Balancing all of the foregoing considerations and thereby developing polymeric compositions with good flame retardant characteristics as well as a satisfactory balance of other properties is, consequently, a task which has in the past and presently continues to require the exercise of a high degree of inventive skill.

SUMMARY OF THE INVENTION

This invention pertains to compounds of the formula $$N\!\!-\!\!\!\left(CH_2P(OR)_2\right)_3 \qquad (I)$$

wherein each R is independently selected from the group comprising halogenated alkyl radicals having from about 2 to about 6 carbon atoms and from 1 to about 4 halogen substituents. Also within the scope of this invention is a polyurethane polymeric composition comprising a polyurethane polymer and a flame retarding amount of the above described compound.

DESCRIPTION OF THE PREFERRED EMBODIMENTS

The flame retarding compounds within the scope of this invention have Formula I above wherein each R is independently selected from the group comprising halogenated alkyl radicals containing from about 2 to about 6 carbon atoms, preferably from about 2 to about 4 carbon atoms, and from 1 to about 4 halogen substituents. Preferably, the halogen substituents are selected from the group comprising chlorine and bromine. It is also preferred that all of the R groups be identical. For purposes of illustration only, Table I is designed to further help describe the compounds of Formula I of this invention and is neither meant nor should it be taken to be a complete listing of all of the compounds within the scope of Formula I.

TABLE I

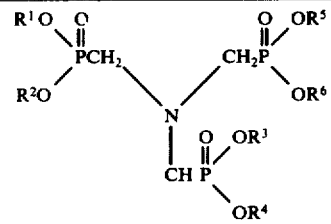

| Compound | |
|---|---|
| 1 | wherein $R^1$ through $R^6$ are each $CH_2CHBrCH_2Br$ |
| 2 | wherein $R^1$ through $R^6$ are each $CH_2CHClCH_2Cl$ |
| 3 | wherein $R^1$ through $R^6$ are each $CH_2CH_2CH_2Br$ |
| 4 | wherein $R^1$ through $R^6$ are each $CH_2CH_2Br$ |
| 5 | wherein $R^1$ through $R^6$ are each $CH_2CHBrCH_3$ |
| 6 | wherein $R^1$ through $R^6$ are each $CH_2CH_2Cl$ |
| 7 | wherein $R^1$ through $R^6$ are each $(CH_2)_5CH_2Br$ |
| 8 | wherein $R^1$ through $R^6$ are each $(CH_2)(CHBr)_3CH_2Br$ |
| 9 | wherein $R^1$ through $R^6$ are each $CH_2CH(CH_2Br)_2$ |
| 10 | wherein $R^1$ is $CH_2CH_2Br$ and $R^2$ through $R^6$ are each $CH_2CHBrCH_2Br$ |
| 11 | wherein $R^1$ through $R^6$ are each $CH_2CHClCH_2Br$ |
| 12 | wherein $R^1$ and $R^2$ are each $CH_2CHBrCH_2Br$ and $R^3$ through $R^6$ are each $CH_2CHClCH_2Cl$ |
| 13 | wherein $R^1$ through $R^6$ are each $CH(CH_2Br)_2$ |
| 14 | wherein $R^1$ through $R^6$ are each $CH(CH_2Cl)_2$ |
| 15 | wherein $R^1$ through $R^6$ are each $CH_2CHClCH_2CCl_3$ |

The following is a partial listing of the preferred compounds within the scope of this invention: bis(2,3-dibromopropyl)nitrilo(trimethylene phosphonate), bis(2,3-dichloropropyl)nitrilo(trimethylene phosphonate), bis(3-bromopropyl)nitrilo(trimethylenephosphonate), bis(3-chloropropyl)nitrilo(trimethylene phosphonate), bis(2-bromoethyl)nitrilo(trimethylene phosphonate), and bis(2-chloroethyl)nitrilo(trimethylene phosphonate).

The compounds within the scope of this invention are prepared according to the general reaction scheme:

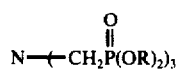

-continued

wherein R is as defined above. In general, two moles of an haloalkanol are added dropwise to phosphorus trichloride. This addition can take place in the presence or absence of a solvent. If a solvent is used, an inert solvent can be employed, e.g., toluene, benzene, ether, etc. The above reaction can be performed at from about 0° to about 35° C. Water is added dropwise to the bis(haloalkyl)chlorophosphite product of the above reaction while keeping the temperature of the reactants at from about 0° to about 15° C. bis(haloalkyl)phosphite is the product of the last reaction. This product is isolated by evaporating the solvent and is used in its crude form in the next step. The next step comprises adding said bis(haloalkyl)phosphite to a solution containing 3 moles of formaldehyde (or an equivalent amount of paraformaldehyde) and one mole of ammonia. This addition should take place at a temperature of from about 40° to about 100° C. The bis(haloalkyl)nitrilo(trimethylene phosphonate) end product is washed with water and dried at a temperature from about 80° to about 120° C. until constant weight is achieved.

The compounds of the present invention are useful as flame retardants in polyurethane polymeric compositions comprising a polyurethane polymer and a flame retarding amount of the above described compounds. Polyurethane polymers embrace not only the rigid and flexible foams but the solid elastomeric compositions. A further description of polyurethane polymers applicable to the present invention may be found in Modern Plastics Encyclopedia, Vol. 52, No. 10A McGraw-Hill, Inc., New York, N.Y. (1975), said publication being incorporated herein in toto by reference. It is also contemplated that the flame retardants of Formula I will possess flame retardant efficacy in foamed polystyrene, polyesters and epoxy compositions.

The flame retardants within the scope of this invention may be incorporated into or applied onto the above polymers by techniques which are standard or known to those skilled in the art. See, for example, J. M. Lyons, "The Chemistry and Use of Fire Retardants", Wiley Inter-science, New York, 1970, and Z. E. Jolles, "Bromine and Its Compounds", Academic Press, New York, 1966.

The amount of flame retardant which is used in the compositions and in the methods of this invention is that amount necessary to produce measurable flame retardancy in the compositions which are so modified. Depending upon the particular compound and the particular polymer with which it is combined, the quantity of flame retardant employed in the compositions and methods of this invention can be of any amount up to about 35 percent or more by weight of the total composition. For most compositions, a flame retardant will comprise from about 1 to about 25 percent by weight of the total composition.

In addition to the flame retardant compounds within the scope of this invention, the flame retardancy of a polymer can be further enhanced through the use of so-called "synergists" or enhancing agents which, when used with the compounds of Formula I, promote a cooperative effect therebetween and thus enhance the flame retardancy of the resultant plastic composition as compared to the flame retardancy of either one component used separately. These "enhancing agents" comprise the oxides and halides of groups IVA and VA of the Periodic Table, and are further described in Modern Plastics Encyclopedia, ibid., as well as U.S. Pat. Nos. 2.993,924; 2,996,528; 3,205,196 and 3,878,165. Without limitation, preferred enhancing agents include $Sb_2O_3$, $SbCl_3$, $SbBr_3$, $SbI_3$, $SbOCl$, $As_2O_3$, $As_2O_5$, $ZnBO_4$, $BaB_2O_4$. $H_2O$, $2.ZnO.3B_2O_3.3.5H_2O$ and stannous oxide hydrate. The more preferred enhancing agent is antimony trioxide.

It is also within the scope of the present invention to employ other materials in the present invention compositions where one so desired to achieve a particular end result. Such materials include, without limitation, adhesion promotors; antioxidants; antistatic agents; antimicrobials; colorants; heat stabilizers; light stabilizers and fillers. The above mentioned materials, including filler, are more fully described in Modern Plastics Encyclopedia, ibid., and which publication has been incorporated herein in toto by reference.

The amount of the above described materials employed in the present invention compositions can be any quantity which will not substantially adversely affect the desired results derived from the present invention compositions. Thus, the amount used can be zero (0) percent, based on the total weight of the composition, up to that percent at which the composition can still be classified as a plastic. In general, such amount will be from about 0% to about 75% and more specifically from about 1% to about 50%.

The following examples are provided for the purpose of further illustration only and are not intended to be limitations on the disclosed invention. Unless otherwise specified, all temperatures are expressed in degrees centigrade; all weights are expressed in grams; and all volumes are expressed in milliliters.

EXAMPLE 1

Preparation of bis(3-bromopropyl)nitrilo(trimethylene phosphonate):

Phosphorus trichloride (137 grams; 1 mole) was dissolved in 100 ml. of methylene chloride and 278 grams (2 moles) of a bromopropanol mixture was added dropwise over a period of 2 hours with stirring and external cooling in ice to keep the temperature below 15° C. Upon complete addition the reaction mixture was warmed to 35° C., held at that temperature for 1 hour, and then cooled again to 10° C. Water (18 grams; 1 mole) was added dropwise keeping the temperature below 15° C. Upon complete addition, excess hydrogen chloride was removed under vacuum and the solution was then heated for 1 hour at 40° C. The methylene chloride was evaporated to yield 319 grams of a colorless oil. Infrared absorption at 2460 cm$^{-1}$ confirmed the bis(3-bromopropyl)phosphite structure.

To 66 grams of a 37 percent aqueous formaldehyde solution (10 percent excess) was added 15 grams of a 29 percent aqueous ammonium solution with stirring. A slight exothermic reaction developed. The solution was allowed to stir for one-half hour and then 250 grams of the above bis(3-bromopropyl)phosphite was added dropwise over a one-hour period. The mixture was stirred at room temperature for an additional 1 hour and then heated to 60° C. and held at that temperature for 8 hours. The organic layer was separated and washed twice with water. The resulting viscous straw-colored oil was dried at 100° C./1.5 mm of mercury for 2 hours. The infrared showed the disappearance of the POH absorption. Analysis for $C_{21}H_{42}Br_6NO_9P_3$: calculated: bromine: 46.8%; phosphorus: 9.08%; Found: bromine: 43.25 %; phosphorus: 9.32%.

EXAMPLE 2

Preparation of bis(2-chloroethyl)nitrilo(trimethylene phosphonate):

Phosphorus trichloride (549 grams; 4 moles) was placed into a 3-liter flask along with 400 ml of methylene chloride. Ethylene oxide (352 grams) was bubbled into the above solution having a temperature of 40° to 60° C. Next, 20 drops of 2-chloroethanol was added as a catalyst. After addition of the ethylene oxide, the mixture was stirred for one-half hour and then cooled to 10° C. Water (72 grams; 4 moles) was added dropwise keeping the temperature below 25° C. The solvent was removed under vacuum leaving a clear liquid. The yield of bis(2-chloroethyl)phosphite was 695 grams or 85%.

Next, 275 grams of a 37% aqueous formaldehyde solution was placed into a separate 3-liter flask. To this latter flask was also added dropwise 66.4 grams (1.13 moles) of a 29% aqueous ammonia solution while keeping the temperature below 35° C. The solution was stirred for one-half hour and then 695 grams (3.4 moles) of the above bis(2-chloroethyl)phosphite was added dropwise keeping the temperature below 35° C. The solution was then heated to 60° C. and held at said temperature while stirring for 5 hours. The material was washed twice with water, washed once with aqueous ammonia, and then with another water wash. The water was removed under vacuum. The material was filtered with celite and celkate. The material was a clear viscous liquid. Yield: 220 grams. Acid number: 0.8 Percent chlorine: theory: 31.6%; found: 32.55%.

Other compounds within the scope of this invention, e.g., bis(2,3-dibromorpopyl)nitrilo(trimethylene phosphonate), bis(2,3-dichloropropanol)nitrilo(trimethylene phosphonate), bis(3-chloropropyl)nitrilo)trimethylene phosphonate), and bis(2-bromoethyl)nitrilo(trimethylene phosphonate), can be prepared in a manner similar to that shown in Examples 1 and 2.

EXAMPLE 3

A rigid foam was prepared using the following basic formulation:

| Component | Parts by Weight |
|---|---|
| Polyol[a] | 100 |
| Silicone Glycol Surfactant[b] | 2 |
| Trichlorofluoromethane[c] | 35 |
| Polyisocyanate[d] | 135 |

[a]alkanolamine polyol, molecular weight approximately 3500, hydroxyl number approximately 530, Thanol R-350-X, Jefferson Chemical Co., Houston, TX.
[b]Dow Corning 193, Dow Corning Corp., Midland, MI.
[c]Freon 11B, E.I. Du Pont de Nemours & Co., Wilmington, DE.
[d]Polymeric aromatic isocyanate, 31.5% available NCO, Mondur MRS, Mobay Chemical Co., Pittsburgh, PA.

The polyol, surfactant, and fluorocarbon blowing agent were combined in a masterbatch based on 1000 gm of polyol to minimize loss of blowing agent.

The following procedure was used to prepare the foam:

1. The polyisocyanate was weighed into a tared, 10 ounce, paper cup (allowances being made for holdup) and the cup set aside while the remaining ingredients were weighed out and mixed.
2. The polyol masterbatch was weighed out, in the proper amount to give 100 grams of polyol, in a one quart, untreated, paper cup.
3. The 10 grams of the flame retardant of Example 1 were then weighed into the same one quart cup.
4. The contents of the one quart cup were mixed at 1000 rpm for 5 seconds.
5. The polyisocyanate was then added and stirring at 1000 rpm continued for 10 seconds.
6. The mix was poured into a 5-pound, untreated, paper tub and allowed to rise.

After the foam was tack-free, and substantially cured, it was set aside for at least 7 days prior to subjecting said foam to an Oxygen Index Test, ASTM D-2863-74, and a Compressive Strength Test, ASTM D-1621-73. The results of said tests are reported in Table II.

The same procedure was used to prepare other rigid foams at different load levels or containing a different flame retardant additive. These foams were also subjected to the same Oxygen Index Test and Compressive Strength Test as the above foam and the data are also reported in Table II.

TABLE II

| Flame Retardant | Load Level, php[a] | OI, percent | Maximum Compressive Strength psi |
|---|---|---|---|
| Control | 0 | 21 | 29.5 |
| Example 1 | 10 | 24.0 | 31.1 |
| | 20 | 25.5 | 34.6 |
| | 30 | 27.0 | 35.3 |
| Example 2 | 30 | 25.0 | |

[a]parts per hundred polyol.

Table II clearly shows that the compounds within the scope of this invention, as exemplified by compounds 3 and 6 of Table I, possess an excellent degree of flame retardant efficacy in polyurethane polymeric compositions and further do not detract from, and in fact help improve, the physical properties of said polymeric compositions. Other flame retardant compounds within the scope of this invention which also display excellent flame retardant efficacy in polyurethane polymeric compositions include bis(2,3-dibromopropyl)nitrilo(-trimethylene phosphonate), bis(2,3-dichloropropyl)nitrilo(trimethylene phosphonate), bis(3-chloropropyl)nitrilo(trimethylene phosphonate), and bis(2,bromoethyl)-nitrilo(trimethylene phosphonate).

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. A flame-retardant polyurethane polymeric composition comprising a polyurethane polymer and a flame retarding amount of a compound of the formula

wherein each R is independently selected from the group comprising halogenated alkyl radicals having from about two to about six carbon atoms and from one to about four halogen substituents.

2. The polyurethane polymeric composition of claim 1 wherein said halogen substituents are selected from the group comprising chlorine and bromine.

3. The polyurethane polymeric composition of claim 2 wherein each of said halogenated alkyl radicals contain from about two to about four carbon atoms.

4. The polyurethane polymeric compositions of claim 2 wherein all R groups are identical.

5. The polyurethane polymeric composition of claim 1 wherein said compound is bis(2,3-dibromopropyl)nitrilo(trimethylene phosphonate), bis(2,3-dichloropropyl)nitrilo(trimethylene phosphonate), bis(3-bromopropyl)nitrilo(trimethylene phosphonate), bis(3-chloropropyl)nitrilo(trimethylene phosphonate), bis(2-bromoethyl)nitrilo(trimethylene phosphonate), and bis(2-chloroethyl)nitrilo(trimethylene phosphonate).

6. A compound of the formula

wherein each R is independently selected from the group comprising halogenated alkyl radicals having from about two to about six carbon atoms and from one to about four halogen substituents.

7. The compound of claim 6 wherein said halogen substituents are selected from the group comprising chlorine and bromine.

8. The compound of claim 7 wherein each of said halogenated alkyl radicals contains from about two to about four carbon atoms.

9. The compound of claim 7 wherein all R groups are identical.

10. The compound of claim 6 selected from the group comprising bis(2,3-dibromopropyl)nitrilo(trimethylene phosphonate), bis(2,3-dichloropropyl)nitrilo(trimethylene phosphonate), bis(3-bromopropyl)nitrilo(trimethylene phosphonate), bis(3-chloropropyl)nitrilo(trimethylene phosphonate), bis(2-bromoethyl)nitrilo(trimethylene phosphonate), and bis(2-chloroethyl)nitrolo(trimethylene phosphonate).

* * * * *